(12) United States Patent
Kasuya

(10) Patent No.: US 9,724,481 B2
(45) Date of Patent: Aug. 8, 2017

(54) GAS DELIVERY SYSTEM AND SURGERY SYSTEM

(71) Applicant: OLYMPUS CORPORATION, Tokyo (JP)

(72) Inventor: Yuma Kasuya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/474,904

(22) Filed: Sep. 2, 2014

(65) Prior Publication Data

US 2014/0371667 A1 Dec. 18, 2014

Related U.S. Application Data

(63) Continuation of application No. PCT/JP2013/067567, filed on Jun. 26, 2013.

(30) Foreign Application Priority Data

Jun. 27, 2012 (JP) .................................. 2012-144766

(51) Int. Cl.
*A61M 13/00* (2006.01)
*A61M 1/00* (2006.01)
(Continued)

(52) U.S. Cl.
CPC ....... *A61M 13/003* (2013.01); *A61B 1/00135* (2013.01); *A61B 1/015* (2013.01);
(Continued)

(58) Field of Classification Search
CPC ............ A61M 1/0064; A61M 5/16827; A61M 5/14566; A61M 5/14244; A61B 1/267
See application file for complete search history.

(56) References Cited

U.S. PATENT DOCUMENTS 4,490,331 A * 12/1984 Steg, Jr. .......................... 422/46
4,519,385 A * 5/1985 Atkinson ............ A61M 1/0064
601/161

(Continued)

FOREIGN PATENT DOCUMENTS

| JP | A-09-122069 | 5/1997 |
| JP | A-2007-75518 | 3/2007 |
| WO | WO 2007/080971 A1 | 7/2007 |

OTHER PUBLICATIONS

International Search Report issued in International Patent Application No. PCT/JP2013/067567 dated Jul. 23, 2013.
(Continued)

*Primary Examiner* — Bhisma Mehta
*Assistant Examiner* — Matthew A Engel
(74) *Attorney, Agent, or Firm* — Oliff PLC

(57) ABSTRACT

A gas delivery system supplying a body cavity with a given gas includes a first guide pipe for supplying the given gas into the body cavity and a second guide pipe installed in the first guide pipe for supplying the given gas into the body cavity at a flow velocity that differs from that of the first guide pipe. A flow velocity of the given gas that is supplied from a first conduit which is formed by the first guide pipe and the second guide pipe is faster than a flow velocity of the given gas that is supplied from a second conduit which is formed in the second guide pipe.

12 Claims, 19 Drawing Sheets

(51) Int. Cl.
*A61B 1/00* (2006.01)
*A61B 1/015* (2006.01)
*A61B 1/313* (2006.01)

(52) U.S. Cl.
CPC ......... *A61B 1/3132* (2013.01); *A61M 1/0023* (2013.01); *A61B 1/00119* (2013.01); *A61M 2205/3379* (2013.01); *A61M 2210/1021* (2013.01)

(56) References Cited

U.S. PATENT DOCUMENTS

| | | | | |
|---|---|---|---|---|
| 4,561,431 | A * | 12/1985 | Atkinson | A61M 3/0258 601/161 |
| 4,599,093 | A * | 7/1986 | Steg, Jr. | 95/46 |
| 4,655,197 | A * | 4/1987 | Atkinson | A61M 1/0058 601/160 |
| 4,669,453 | A * | 6/1987 | Atkinson | A61M 1/0058 433/80 |
| 4,715,372 | A * | 12/1987 | Philippbar et al. | 606/2 |
| 5,152,746 | A * | 10/1992 | Atkinson | A61M 3/0258 604/245 |
| 5,647,852 | A * | 7/1997 | Atkinson | A61M 1/0058 417/360 |
| 5,840,016 | A | 11/1998 | Kitano et al. | |
| 6,497,687 | B1 * | 12/2002 | Blanco | A61B 17/3494 604/164.01 |
| 6,716,201 | B2 * | 4/2004 | Blanco | A61B 17/3494 604/164.01 |
| 6,719,746 | B2 * | 4/2004 | Blanco | A61B 17/3494 604/164.01 |
| 7,476,213 | B2 * | 1/2009 | Uesugi et al. | 604/26 |
| 7,569,027 | B2 * | 8/2009 | Uesugi et al. | 604/23 |
| 7,722,559 | B2 * | 5/2010 | Uesugi et al. | 604/26 |
| 7,854,724 | B2 * | 12/2010 | Stearns | A61B 17/3421 604/164.01 |
| 7,981,072 | B2 * | 7/2011 | Uesugi et al. | 604/23 |
| 7,988,656 | B2 * | 8/2011 | Uesugi et al. | 604/23 |
| 8,231,523 | B2 * | 7/2012 | Uesugi et al. | 600/118 |
| 8,381,729 | B2 * | 2/2013 | Freitag | A61M 16/16 128/207.14 |
| 8,734,381 | B2 * | 5/2014 | Noda et al. | 604/26 |
| 8,840,580 | B2 * | 9/2014 | Uesugi et al. | 604/26 |
| 9,144,396 | B2 * | 9/2015 | Choe | A61B 5/097 |
| 2005/0217727 | A1 * | 10/2005 | Uesugi et al. | 137/315.01 |
| 2005/0222491 | A1 * | 10/2005 | Noda et al. | 600/104 |
| 2005/0222534 | A1 * | 10/2005 | Uesugi et al. | 604/26 |
| 2005/0222535 | A1 * | 10/2005 | Uesugi et al. | 604/26 |
| 2005/0234391 | A1 * | 10/2005 | Uesugi et al. | 604/24 |
| 2006/0004322 | A1 * | 1/2006 | Uesugi et al. | 604/26 |
| 2006/0030751 | A1 * | 2/2006 | Uesugi et al. | 600/101 |
| 2006/0058617 | A1 * | 3/2006 | Sano et al. | 600/407 |
| 2006/0129087 | A1 * | 6/2006 | Uesugi et al. | 604/26 |
| 2007/0088275 | A1 * | 4/2007 | Stearns | A61B 17/3421 604/164.01 |
| 2007/0163585 | A1 * | 7/2007 | Uesugi et al. | 128/204.18 |
| 2007/0244363 | A1 * | 10/2007 | Sano et al. | 600/158 |
| 2010/0106080 | A1 * | 4/2010 | Uesugi et al. | 604/26 |
| 2011/0021942 | A1 * | 1/2011 | Choe | A61B 5/097 600/532 |
| 2011/0125084 | A1 * | 5/2011 | Stearns | A61B 17/3421 604/26 |
| 2012/0184897 | A1 * | 7/2012 | Poll | A61B 1/015 604/24 |
| 2013/0303852 | A1 * | 11/2013 | Hiraga et al. | 600/118 |
| 2014/0303550 | A1 * | 10/2014 | Williams et al. | 604/26 |
| 2014/0371667 | A1 * | 12/2014 | Kasuya | 604/26 |

OTHER PUBLICATIONS

Notice of Rejection Grounds issued in Japanese Patent Application No. 2013-553556 dated Feb. 18, 2014 (with translation).
Opinion against International Search Report issued in International Patent Application No. PCT/JP2013/067567 dated Jul. 23, 2013 (with translation).

\* cited by examiner

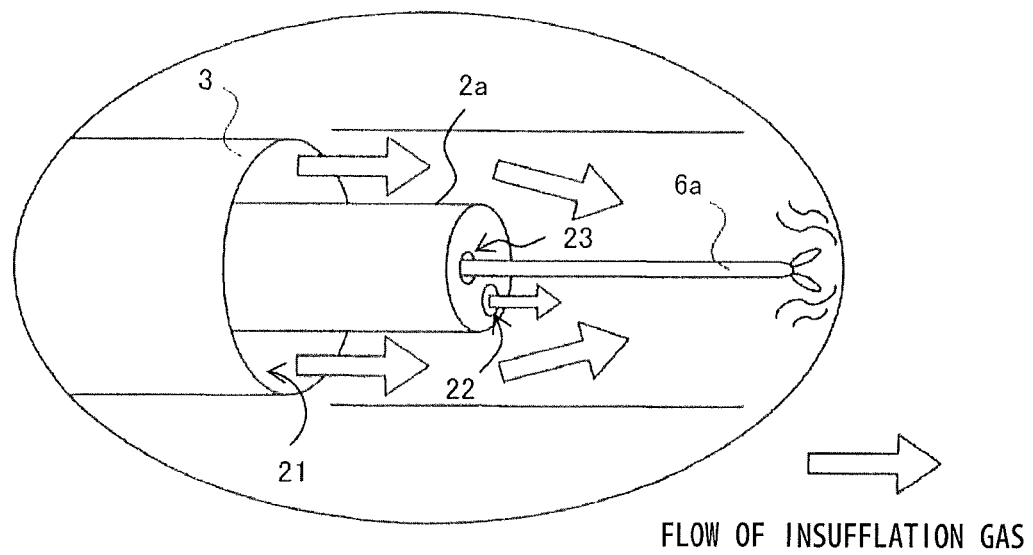
F I G. 2

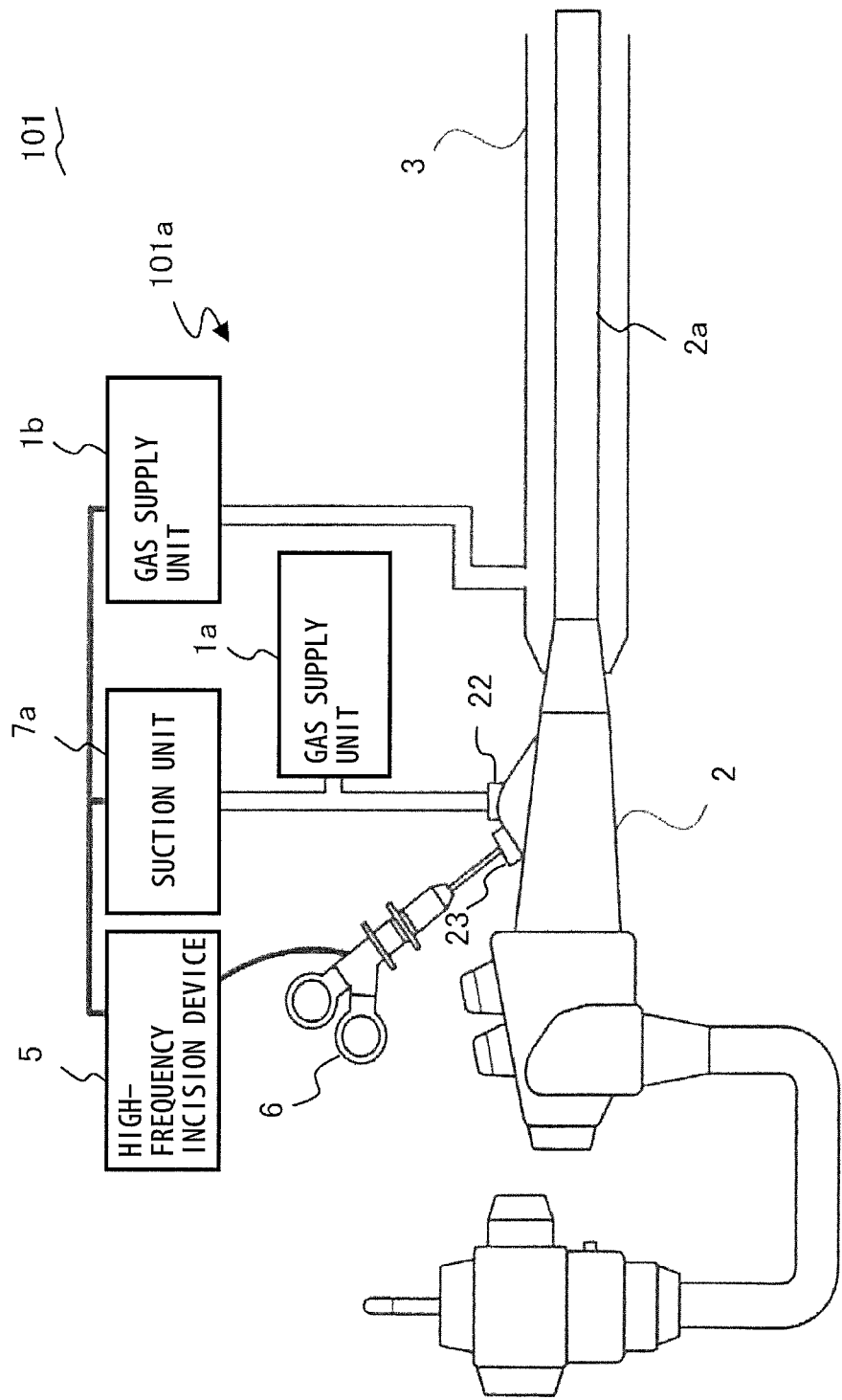
F I G. 4

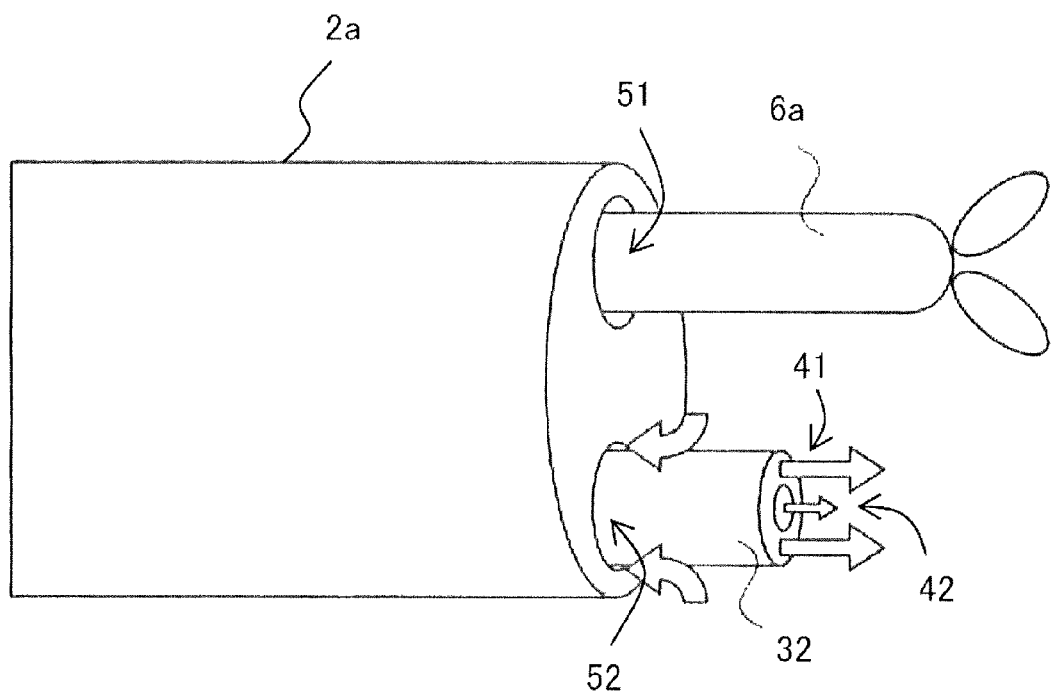
F I G. 7

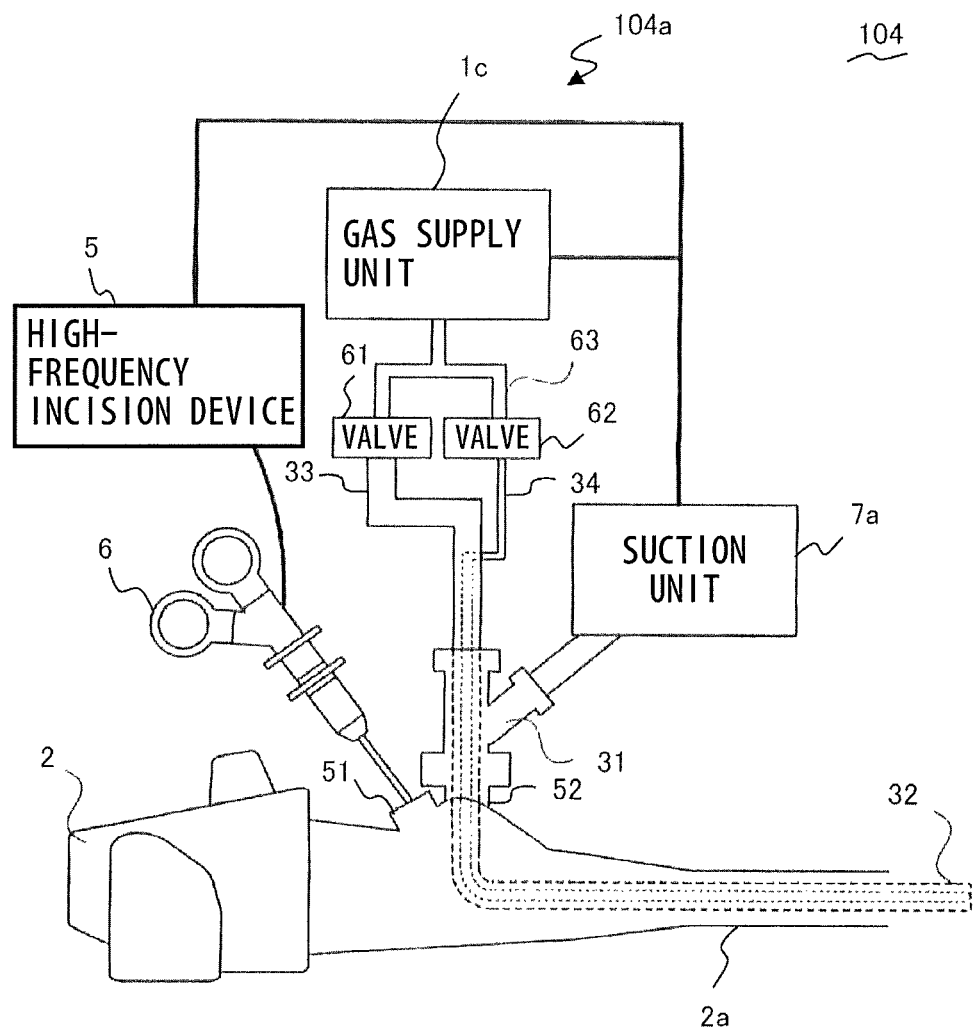
F I G. 9

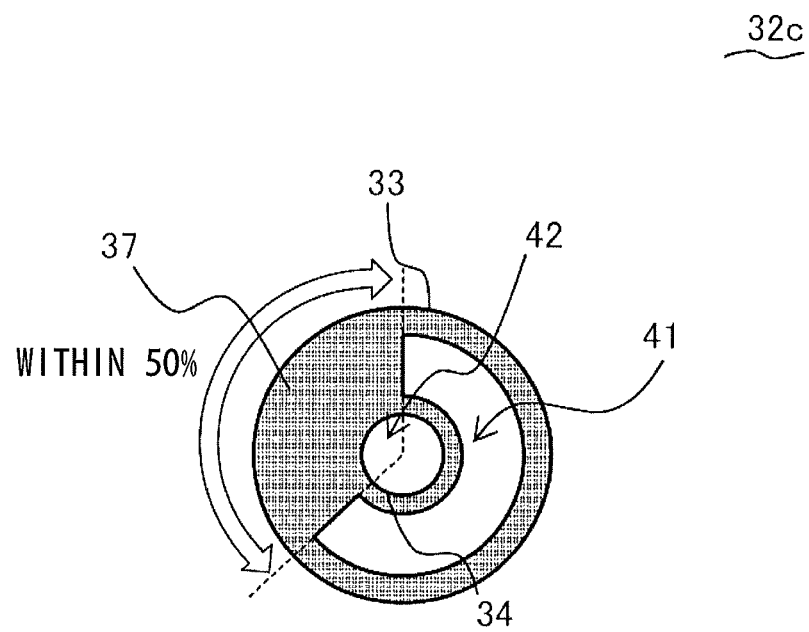
F I G. 12

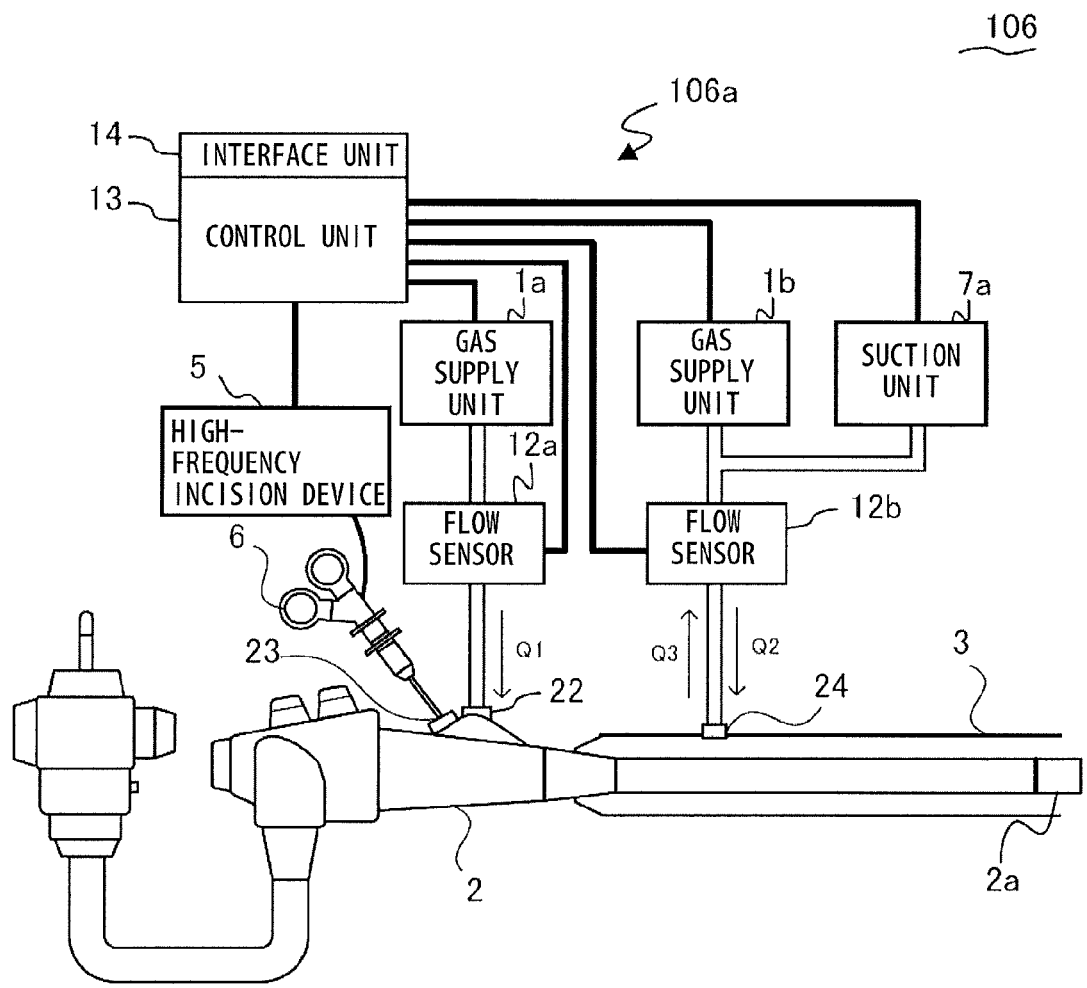
F I G. 16

US 9,724,481 B2

GAS DELIVERY SYSTEM AND SURGERY SYSTEM

CROSS-REFERENCE TO RELATED APPLICATIONS

This application is based upon and claims the benefit of priority of the prior Japanese Patent Application No. 2012-144766, filed Jun. 27, 2012, the entire contents of which are incorporated herein by reference. This is a Continuation Application of PCT Application No. PCT/JP2013/067567, filed Jun. 26, 2013, which was not published under PCT Article 21 (2) in English.

FIELD

The embodiments discussed herein are related to a gas delivery system and a surgery system, and particularly are related to a gas delivery system for medical use which is used, for example, in gastrointestinal endoscopic surgery.

BACKGROUND

In gastrointestinal endoscopic surgery, the supplying of gas to the body cavity for ensuring a visual field for the endoscope and aspiration from the body cavity for removal of filth, degassing and discharging of fumes are frequently performed. These are performed via button operations by a surgeon.

In recent years, in order to reduce the operation burden on the surgeon, which has been increasing with the advancement of endoscopic surgery technique, attempts to automate gas supply and aspiration have been studied. For example, it is conceivable that an automation technology for the gas supply and aspiration in laparoscopic surgery that has already been put into practical use can be applied to gastrointestinal endoscopic surgery.

International Publication Pamphlet No. WO 2007-080971 discloses a gas delivery system which is applicable to gastrointestinal endoscopic surgery in which pressure in the stomach is controlled in relation to the pressure in the abdominal cavity on the basis of the pressure value from the pressure sensor.

SUMMARY

One aspect of the disclosure provides a gas delivery system for supplying a given gas to the body cavity, that includes a first guide pipe to be inserted into the body cavity for supplying the given gas into the body cavity and a second guide pipe installed in the first guide pipe for supplying the given gas into the body cavity at a flow velocity that differs from that of the first guide pipe. A flow velocity of the given gas that is supplied from a first conduit which is formed by the first guide pipe and the second guide pipe is faster than a flow velocity of the given gas that is supplied from a second conduit which is formed in the second guide pipe.

Another aspect of the disclosure provides a surgery system including the gas delivery system as described in the aspect above and a suction unit connected to the gas delivery system.

BRIEF DESCRIPTION OF THE DRAWINGS

The present disclosure will be more apparent from the following detailed descriptions when the accompanying drawings are referenced.

FIG. 2 is a partially enlarged view of the surgery system according to the first embodiment;

FIG. 4 is a diagram illustrating a portion of a configuration of a modification of the surgery system according to the first embodiment;

FIG. 7 is a partially enlarged view of the surgery system according to the second embodiment;

FIG. 9 is a diagram illustrating a portion of a modification of the surgery system according to the second embodiment;

FIG. 12 is a section view of a gas supply beam probe of a modification of the surgery system according to the fourth embodiment;

FIG. 16 is a diagram illustrating a portion of a configuration of a surgery system according to a sixth embodiment;

DESCRIPTION OF EMBODIMENTS

In gastrointestinal endoscopic surgery, unlike laparoscopic surgery, supplying of gas and aspiration is performed endoscopically from positions close to each other in a narrow body cavity such as the gastrointestinal tract. Therefore, a supplied gas is easily aspirated. Accordingly, there are a lot of cases in which it is difficult for the supplied gas to reach the affected part just through application of an automation technology for gas supply and aspiration used in laparoscopic surgery to a gas delivery system used for gastrointestinal endoscopic surgery.

When the supplied gas does not reach the affected area, because the fumes from the affected area being treated are not being sufficiently circulated by the supplied gas, a discharge of fumes through aspiration is not performed effectively. Therefore, a good visual field in the body cavity cannot be ensured. The following describes the embodiments of the present disclosure.

<First Embodiment>

Figure 1:
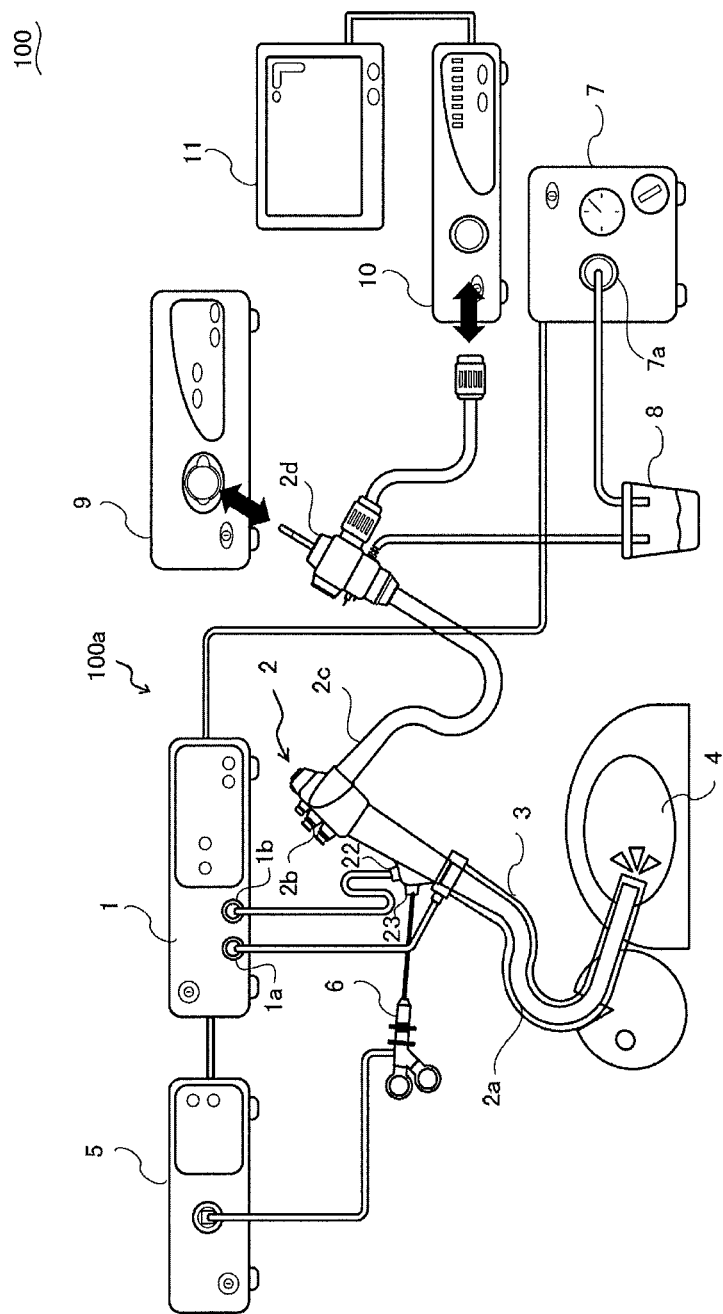
FIG. 1 is a diagram illustrating a configuration of a surgery system according to a first embodiment.
Figure 3:
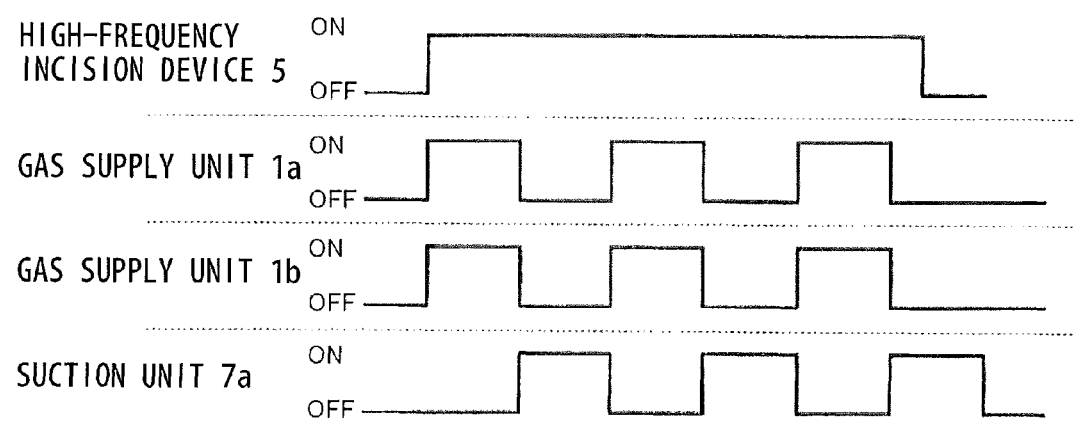
FIG. 3 is a diagram for explaining an operation timing of various devices of the surgery system according to the first embodiment.

FIG. 1 is a diagram illustrating a configuration of a surgery system 100 according to the present embodiment. FIG. 2 is an enlarged diagram of the surgery system 100 according to the present embodiment. FIG. 3 is a diagram for explaining an operation timing of various devices of the surgery system 100 according to the present embodiment.

The surgery system 100 according to the present embodiment is a surgery system used in gastrointestinal endoscopic surgery for example, having a gas supply function to supply an insufflation gas of a given gas to a body cavity. The surgery system 100, as illustrated in FIG. 1, includes a gas supply device 1, a gastrointestinal endoscope 2, an overtube 3, a high-frequency incision device 5, a treatment instrument 6, an aspirator 7, a suction flask 8, a light source device 9, a video processor 10, and a monitor 11. Of the surgery system 100, mainly the gas supply device 1, the gastrointestinal endoscope 2, and the overtube 3 constitute the gas delivery system 100a implementing a gas supply function. The gas delivery system 100a is connected to the high-frequency incision device 5 and the aspirator 7.

The gas supply device 1 is structured as a gas supply unit to supply the gastrointestinal endoscope 2 and the overtube 3 with an insufflation gas supplied from a not-illustrated gas cylinder. The gas supply device 1, which is a gas supply unit, includes a gas supply unit 1a to supply the overtube 3 with the insufflation gas and a gas supply unit 1b to supply the gastrointestinal endoscope 2 with insufflation gas. As the insufflation gas, a gas such as carbon dioxide may be used. As will be described later, the gas supply device 1 is configured in conjunction with the operation of a high-frequency incision device 5 and the aspirator 7, which are electrically connected with each other so as to automatically supply the insufflation gas.

The gastrointestinal endoscope 2 is a flexible endoscope formed with two channels and includes an insertion portion 2a which is inserted through the overtube 3 into the gastrointestinal lumen 4 such as the esophagus, the stomach and the colon. The gastrointestinal endoscope 2 further includes an operation section 2b for the surgeon to operate, a universal cord portion 2c, and a connector portion 2d to be connected to the light source device 9.

The two channels (channel 22, channel 23) formed in the gastrointestinal endoscope 2 are common channels, which are provided for the use of treatment instruments. However, in the surgery system 100, channel 22 of one of the channels of the gastrointestinal endoscope 2 is connected to a tube linked to the gas supply unit 1b of the gas supply device 1. As illustrated in FIG. 2, the insufflation gas introduced into the channel 22 through the tube from the gas supply unit 1b is supplied to the gastrointestinal lumen 4 from the distal end of the insertion portion 2a. The channel 23 on the other hand is inserted with the treatment instrument 6, which is electrically connected to the high-frequency incision device 5, and as illustrated in FIG. 2, the high-frequency probe 6a is inserted into the gastrointestinal lumen 4 from the distal end of the insertion portion 2a.

To the connector portion 2d of the gastrointestinal endoscope 2, a tube that links to the suction flask 8 is connected. To the suction flask 8, a tube linked to the suction unit 7a of the aspirator 7 is further connected. The tube, which is connected to the connector portion 2d is linked with the channel 22 inside the gastrointestinal endoscope 2. To the connector portion 2d is further linked a scope cable connected to the video processor 10.

The overtube 3 is used to guide the insertion portion 2a of the gastrointestinal endoscope 2 into the gastrointestinal lumen 4 of the patient. To the overtube 3, a tube linked to the gas supply unit 1a of the gas supply device 1 is connected. The same gas as the gas introduced into the channel 22 is introduced into the internal portion of the overtube 3 from the gas supply unit 1a. In the surgery system 100, the gastrointestinal endoscope 2 side of the overtube 3 is sealed in a state with the insertion portion 2a of the gastrointestinal endoscope 2 inserted through the overtube 3. Therefore, the insufflation gas introduced into the overtube 3 through the tube from the gas supply unit 1a passes through a conduit 21 formed by the overtube 3 and the insertion portion 2a of the gastrointestinal endoscope 2, and is supplied to the gastrointestinal lumen 4 as illustrated in FIG. 2.

The high-frequency incision device 5 is a device for supplying energy to the treatment instrument 6. The high-frequency incision device 5 is electrically connected to the gas supply device 1 and the aspirator 7. As will be described later, the operation of the high-frequency incision device 5 functions as a trigger for the operation of the gas supply device 1 and the aspirator 7.

The treatment instrument 6 is a treatment instrument provided with a high-frequency probe 6a at the distal end, and is supplied with energy from the high-frequency incision device 5. The treatment instrument 6 is inserted into the channel 23 of the gastrointestinal endoscope 2 and is used for ablation treatment and the like of the affected area through the high-frequency probe 6a protruding from the insertion portion 2a of the gastrointestinal endoscope 2.

The aspirator 7 is a device for generating a suction pressure. The suction flask 8 is a container for storing aspirates sucked from the gastrointestinal lumen 4 by aspiration operation of the aspirator 7. The aspirator 7 is configured such that it sucks aspirated blood and filth sucked from the gastrointestinal lumen 4 via the channel 22 formed in the gastrointestinal endoscope 2 in conjunction with the operation of the high-frequency incision device 5 and the gas supply device 1 that are electrically connected.

The light source device 9 is provided with an illumination lamp therein. The light source device 9 is connected to the connector portion 2d of the gastrointestinal endoscope 2 and irradiates the gastrointestinal lumen 4 with illumination light from the illumination lamp through a light guide (not shown) provided in the gastrointestinal endoscope 2. The video processor 10 and the monitor 11 are devices for displaying images of the gastrointestinal lumen 4 obtained by the gastrointestinal endoscope 2. The video processor 10 performs signal processing for converting an electrical signal from the image sensor of the gastrointestinal endoscope 2 to a video signal. The monitor 11 displays the received video signal of the endoscopic image.

The surgery system 100 and the gas delivery system 100a thus configured as described above are provided with the overtube 3, which is the first guide pipe inserted into the gastrointestinal lumen 4, and the insertion portion 2a of the gastrointestinal endoscope 2, which is the second guide pipe provided in the overtube 3, as an guide pipe to provide insufflation gas at different flow velocities to the gastrointestinal lumen 4, respectively. In addition, in the surgery system 100 and the gas delivery system 100a, in order for the flow velocity of the insufflation gas supplied from the conduit 21, which is the first conduit formed by the overtube 3 and the insertion portion 2a of the gastrointestinal endoscope 2, to be faster than the flow velocity of the insufflation gas supplied from the channel 22, which is a second conduit that is formed in the insertion portion 2a of the gastrointestinal endoscope 2, the gas supply device 1 supplies and sends insufflation gas to the first conduit (conduit 21) and the second conduit (channel 22).

Therefore, as illustrated in FIG. 2, a difference in pressure is caused by the difference in the flow velocity of the insufflation gas from the conduit 21 and the insufflation gas from the channel 22, and the insufflation gas from the conduit 21 is pulled inwardly. With this, the diffusion of the insufflation gas is suppressed to achieve a high linearity in the insufflation gas as a whole, thereby allowing the insufflation gas to be supplied to a greater distance. Therefore, according to the surgery system 100 and the gas delivery system 100a, it is possible to make the supplied insufflation gas that is supplied to the narrow gastrointestinal lumen 4 reach the affected area more reliably.

Further, by operating the gas supply device 1 (gas supply unit 1a, gas supply unit 1b), the high-frequency incision device 5 and the aspirator 7 (suction unit 7a) in the surgery system 100 in conjunction with each other, the gas supply and aspiration are automated. Specifically, the surgeon triggers the initiation of the cautery treatment by turning the high-frequency incision device 5 to the ON state, whereby the gas supply and aspiration are automatically started. As illustrated in FIG. 3, when the high-frequency incision device 5 is turned to the ON state, the gas supply unit 1a and the gas supply unit 1b are turned to the ON state, starting the gas supply to the gastrointestinal endoscope 2 and the overtube 3. After the gas supply has continued for a certain time, the gas supply unit 1a and the gas supply unit 1b are turned to the OFF state and the suction unit 7a is turned to the ON state, starting the aspiration. Thereafter, when the aspiration has continued for a certain time, the suction unit 7a is turned to the OFF state and the gas supply unit 1a and the gas supply unit 1b are turned to the ON state, resuming gas supply. The above operation is repeated until the high-frequency surgical apparatus 5 is turned to the OFF state.

That is, the gas delivery system 100a is configured to trigger the operation of the high-frequency incision device 5 connected to the gas system 100a to alternatively perform the aspiration of objects in the gastrointestinal lumen 4 by the suction unit 7a, which is connected to the gas delivery system 100a, and the supplying of insufflation gas into the gastrointestinal lumen 4. Therefore, with the surgery system 100 and the gas delivery system 100a, since the supplying of gas and the aspiration are performed alternately by simply operating the high-frequency incision device 5 by the surgeon, it is possible to reduce the operation load of the surgeon.

Further, since the supplying of gas and the aspiration are performed alternately in the surgery system 100, as described above, aspiration of fumes produced by cautery treatment is performed with the fumes diffused by the insufflation gas. Therefore, according to the surgery system 100, fumes can be effectively discharged even when the aspiration position (i.e., the distal end of the overtube 3) is in a location remote from the affected area, and a good visual field of the endoscope can be ensured. Further, performing supplying of gas and aspiration alternately enables the same route to be used for both the gas supply and the aspiration. Therefore, the surgery system 100 uses the channel 22 for both gas supply and aspiration.

Further, in the surgery system 100, the gastrointestinal endoscope 2 and the overtube 3 form a double structure that supplies insufflation gas at different flow velocities. In particular, because the channel 22 of the gastrointestinal endoscope 2 is used as the inner conduit (the second conduit), an existing endoscope instead of a dedicated endoscope can be used if an endoscope having two channels or more in combination with the treatment instrument can be performed. Therefore, it is possible to construct the surgery system 100 by modifying the existing surgery system.

It should be noted that the surgery system 100 and the gas delivery system 100a may be modified in various ways. For example, FIG. 1 illustrates an example in which the suction unit 7a aspirates objects (e.g. , gaseous bodies such as smoke, blood, filth etc.) in the gastrointestinal lumen 4 through the channel 22 and the universal cord section 2c. However, the suction unit 7a may aspirate objects in the gastrointestinal lumen 4 without using the universal cord portion 2c.

Figure 5:
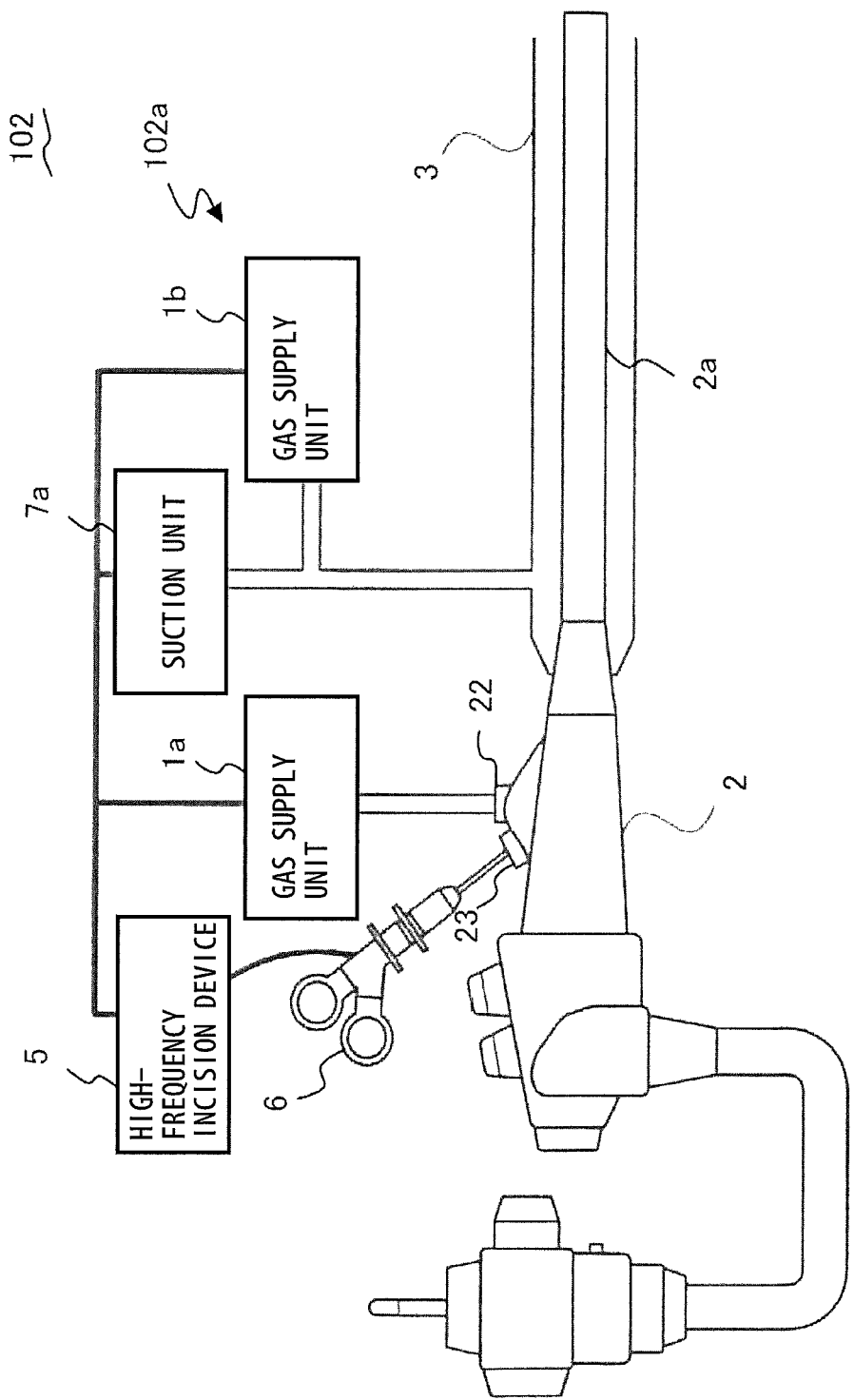
FIG. 5 is a diagram illustrating a portion of a configuration of another modification of the surgery system according to the first embodiment.

FIGS. 4 and 5 are diagrams illustrating a portion of a configuration of a modification of the surgery system according to the present embodiment. As illustrated in FIG. 4, a tube for connecting the gas supply unit 1a with the gastrointestinal endoscope 2 may be further connected to the suction unit 7a. Also, as illustrated in FIG. 5, a tube for connecting the gas supply unit 1b with the overtube 3 may be further connected to the suction unit 7a. Also, according to the surgery systems illustrated in FIGS. 4 and 5 (surgery system 101, surgery system 102) and the gas delivery systems (gas delivery system 101a, gas delivery system 102a), the same effect as in the surgery system 100 and the gas delivery system 100a can be obtained by performing alternately supplying of gas and aspiration. Further, since at minimum only one of the routes used for gas supply needs to be used for the aspiration, the above-mentioned suction unit 7a may be connected to both of the two tubes.

<Second Embodiment>

Figure 6:
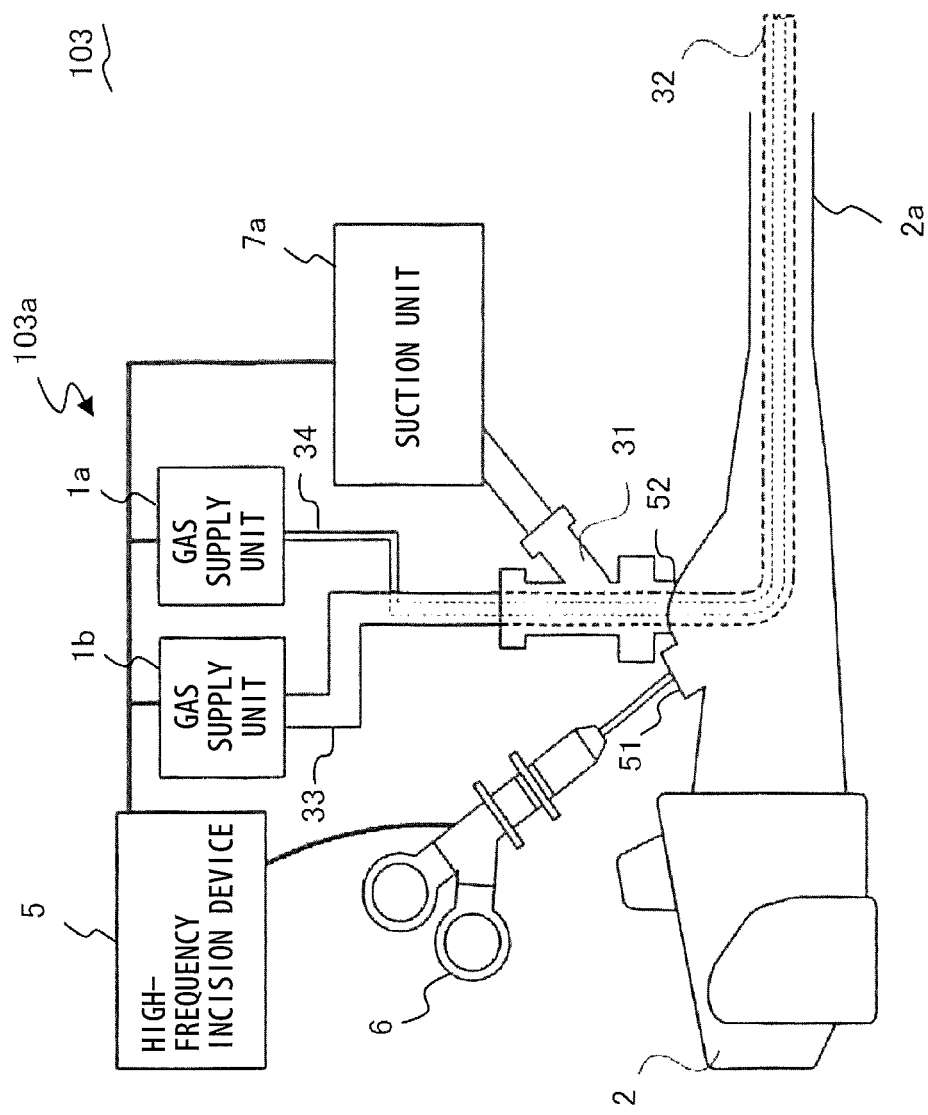
FIG. 6 is a diagram illustrating a portion of a configuration of a surgery system according to a second embodiment.
Figure 8:
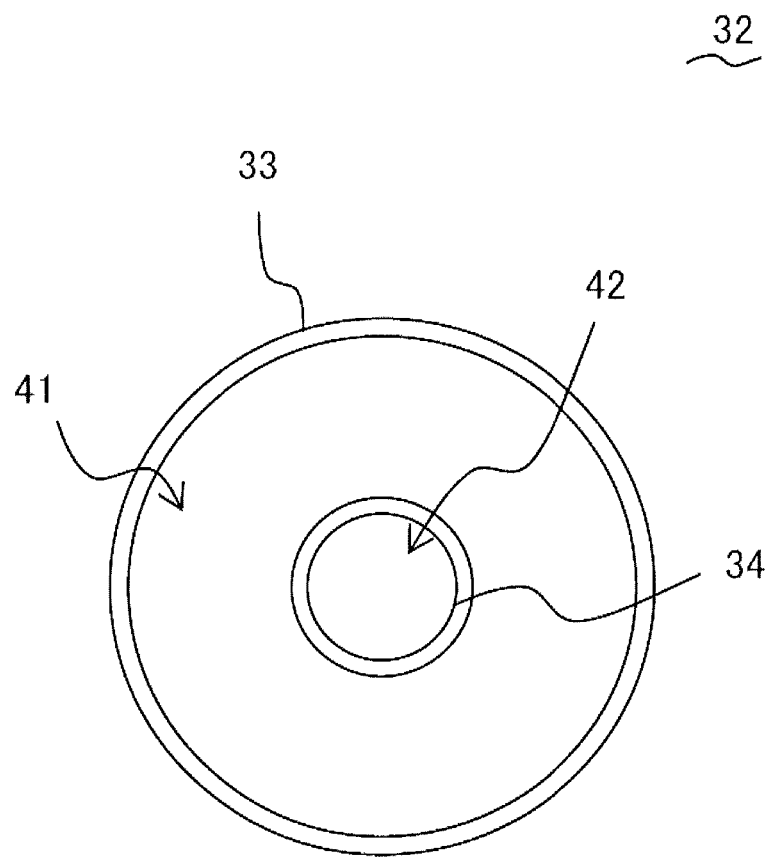
FIG. 8 is a section view of a gas supply beam probe of the surgery system according to the second embodiment.

FIG. 6 is a diagram illustrating a portion of a configuration of a surgery system 103 according to the present embodiment. FIG. 7 is a partially enlarged view of the surgery system 103 according to the present embodiment. FIG. 8 is a sectional view of a gas supply beam probe of the surgery system 103 according to the present embodiment.

The surgery system 103 according to the present embodiment is similar to the surgery system 100 according to the first embodiment in that it includes the gastrointestinal endoscope 2 that is a flexible endoscope in which two channels are formed, and in that a channel 51 of one of the channels in the gastrointestinal endoscope 2 is inserted with the treatment instrument 6 which is electrically connected to the high-frequency incision device 5, and, as illustrated in FIG. 7, the high-frequency probe 6a is inserted into the gastrointestinal lumen from the distal end of the insertion section 2a.

The surgery system 103 differs from the surgery system 100 in that a T-shaped adapter 31 is inserted into another channel 52 of the channels of the gastrointestinal endoscope 2, in that a tube linked to the suction unit 7a is connected to one of the opening portions of the T-shaped adapter 31 which is inserted into the channel 52, and in that a gas supply beam probe 32 is inserted into the channel 52 from the other opening of the T-shaped adapter 31 which is inserted into the channel 52. The surgery system 103 further differs from the surgery system 100 in that it does not include the overtube 3.

In the present embodiment, of the surgery system 103, primarily the gas supply device (the gas supply unit 1a and the gas supply unit 1b) and the gas supply beam probe 32 constitute the gas delivery system 103a that implements the function of supplying gas. The surgery system 103 is further similar to the surgery system 100 in that the surgery system 103 is configured such that the gas supply unit 1a and the gas supply unit 1b provided in the gas supply device are also electrically connected to the high-frequency incision device 5 and the suction unit 7a, and that insufflation gas is automatically supplied in conjunction with the operation of the high-frequency surgical apparatus 5 and the suction unit 7a.

As illustrated in FIGS. 6 and 8, the gas supply beam probe 32 has a dual structure provided with an outer tube 33, which is a first guide pipe extending from the gas supply unit 1b, and an inner tube 34, which is a second guide pipe extending from the gas supply unit 1a. That is, the outer tube 33 and the inner tube 34 are inserted into the channel 52.

In the surgery system 103 and the gas delivery system 103a configured as described above, the gas supply unit 1a and the gas supply unit 1b supply and send insufflation gas to a conduit and a conduit 42 such that the flow velocity of the insufflation gas supplied from the conduit 41 formed between the outer tube 33 and the inner tube 34 is faster than the flow velocity of the insufflation gas supplied from the conduit 42 formed inside the inner tube 34.

Therefore, as is illustrated in FIG. 7, a difference in pressure is caused in the gastrointestinal lumen by the difference in the flow velocity of the insufflation gas from the conduit 41 and the insufflation gas from the conduit 42, and insufflation gas from the conduit 41 is pulled inwardly.

With this, the diffusion in the insufflation gas is suppressed to achieve a high linearity in the insufflation gas as a whole, thereby allowing the insufflation gas to be supplied to a greater distance. Therefore, according to the surgery system 103 and the gas delivery system 103a, it is possible to make the supplied insufflation gas that is supplied to the narrow gastrointestinal lumen reach the affected area more reliably in the same manner as the surgery system 100 and the gas delivery system 100a according to first embodiment.

Further, by operating the gas supply unit 1a and the gas supply unit 1b, the high-frequency incision device 5, and the suction unit 7a in the surgery system 103 in conjunction with each other, the gas supply and aspiration are automated in the same manner as in the surgery system 100. Therefore, with the surgery system 103 and the gas delivery system 103a, since the supplying of gas and aspiration are performed alternately by simply operating the high-frequency incision device 5 by the surgeon, it is possible to reduce the operation load of the surgeon.

Similarly to the surgery system 100 according to the first embodiment, the surgery system 103 may be operated such that the supplying of gas and aspiration are performed alternately. With this, an effective discharge of fumes becomes possible and it is possible to ensure a good visual field for the endoscope. Further, in the surgery system 103, the objects in the gastrointestinal lumen are aspirated from the conduit formed between the insertion portion 2a and the gas supply beam probe 32, that is, from different conduit than the conduits used for supplying gas (conduit 41, conduit 42). Therefore, the surgery system 103 is not limited to the operation pattern for alternately performing supplying of gas and aspiration, but may operate in various ways. For example, supplying of gas and aspiration can temporarily be performed in an overlapping manner. In this case, considering a time lag from the start of supplying of gas (or aspiration) until the actual operation of the supplying of gas (or aspiration), the gas supply unit 1a and the gas supply unit 1b can be operated together with the suction unit 7a. Further, the surgery system 103 is similar to the surgery system 100 according to the first embodiment in that it is possible to make use of the existing endoscope with two or more channels.

FIG. 9 is a diagram illustrating a portion of a configuration of a modification of the surgery system according to the present embodiment. The surgery system 104 and the gas delivery system 104a illustrated in FIG. 9 differ from the surgery system 103 and the gas delivery system 103a in that they include a single gas supply unit 1c instead of the gas supply unit 1a and the gas supply unit 1b, in that the outer tube 33 and the inner tube 34 of the gas supply beam probe 32 are connected together to the gas supply unit 1c by a Y-shaped tube 63, in that they include a valve 61 on the route leading to the outer tube 33 from the gas supply unit 1c of the Y-shaped tube 63, and in that they include a valve 62 on the route leading to the outer tube 34 from the gas supply unit 1c of the Y-shaped tube 63.

The valve 61 is for adjusting the flow velocity of the insufflation gas to be supplied to the gastrointestinal lumen from the conduit 41 formed between the outer tube 33 and the inner tube 34. The valve 62 is for adjusting the flow velocity of the insufflation gas to be supplied to the gastrointestinal lumen from the conduit 42 formed in the inner tube 34. The diameter of the valve 62 is arranged to be smaller than the diameter of the valve 61.

In the surgery system 104 and the gas delivery system 104a configured as described above, the valve 61 and the valve 62 are adjusted such that the flow velocity of the insufflation gas supplied from the conduit 41 formed between the outer tube 33 and the inner tube 34 is faster than the flow velocity of the insufflation gas supplied from the conduit 42 formed in the inner tube 34, thus the same effect can be obtained as in the surgery system 103 and the gas delivery system 103a according to the second embodiment.

Note that in FIG. 9, the Y-shaped tube 63 is formed such that the route leading to the valve 62 and the route leading to the valve 61 have about the same thickness, but the flow velocity of the insufflation gas from the conduit 41 and the flow velocity of the insufflation gas from the conduit 42 may be made different by varying the thickness of the routes. In this case, it is possible to omit the valves 61 and 62.

<Third Embodiment>

Figure 10:
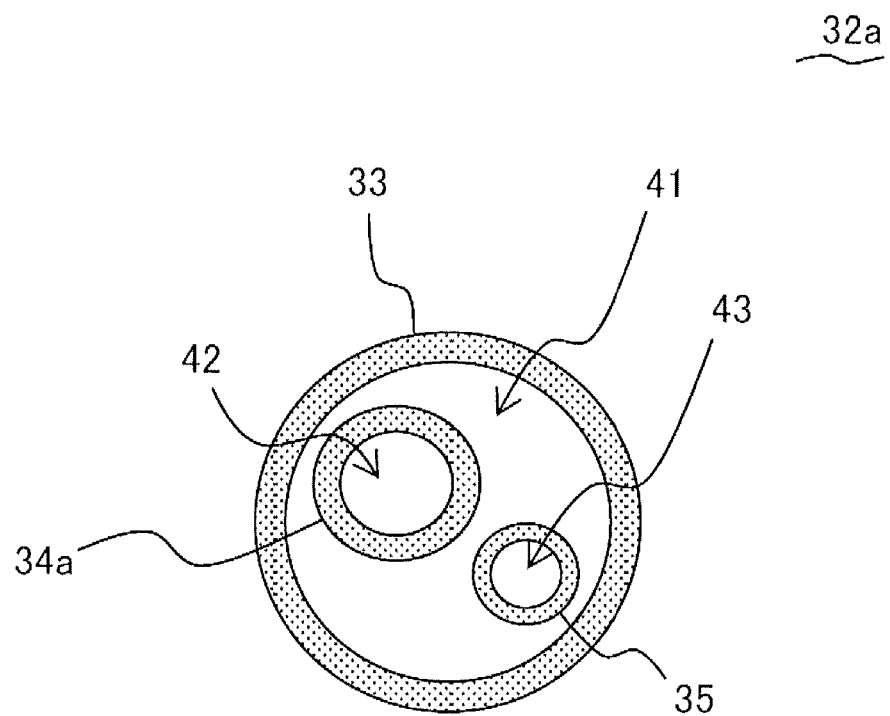
FIG. 10 is a section view of a gas supply beam probe of a surgery system according to a third embodiment.

FIG. 10 is a sectional view of a gas supply beam probe 32a of the surgery system according to the present embodiment. The surgery system according to the present embodiment differs from the surgery system 103 according to the second embodiment in that it includes a water supply/suction unit which performs supplying of water and aspiration in place of the suction unit 7a and in that it includes a gas supply beam probe 32a illustrated in FIG. 10 instead of the gas supply beam probe 32.

The gas supply beam probe 32a is similar to the gas supply beam probe 32 according to the second embodiment in that the outer tube 33 which is a first guide pipe extending from the gas supply unit 1b and the inner tube 34a which is a second guide pipe extending from the gas supply unit 1a are inserted into the channel 52. As illustrated in FIG. 10, the gas supply beam probe 32a is different from the gas supply beam probe 32 according to the second embodiment in that the inner tube 34a is arranged in a position shifted away from the central position of the outer tube 33, and in that it includes an inner tube 35, which is a third guide pipe extending from the water supply/suction unit in a space created by shifting the inner tube 34a away from the central position of the outer tube 33.

In the surgery system and the gas delivery system according to the present embodiment provided with the gas supply beam probe 32a, the gas supply unit 1a and the gas supply unit 1b supply and send insufflation gas to the conduit 41 and the conduit 42 such that the flow velocity of the insufflation gas supplied from the conduit 41 formed between the outer tube 33 and the inner tube 34a is faster than the flow velocity of the insufflation gas supplied from the conduit 42 formed inside the inner tube 34a.

Also, with the surgery system and the gas delivery system according to the present embodiment as described above, the same effect can be obtained as in the surgery system 103 and the gas delivery system 103a according to second embodiment.

Furthermore, according to the surgery system and the gas delivery system according to the present embodiment, by changing the installation position of the inner tube 34a in the outer tube 33, it is possible to effectively utilize the space inside the outer tube 33. Thus, for example, it is possible to supply water to the affected area and perform aspiration of objects in the gastrointestinal lumen from the conduit 43 formed in the inner tube 35, which is provided additionally in the outer tube 33.

<Fourth Embodiment>

Figure 11:
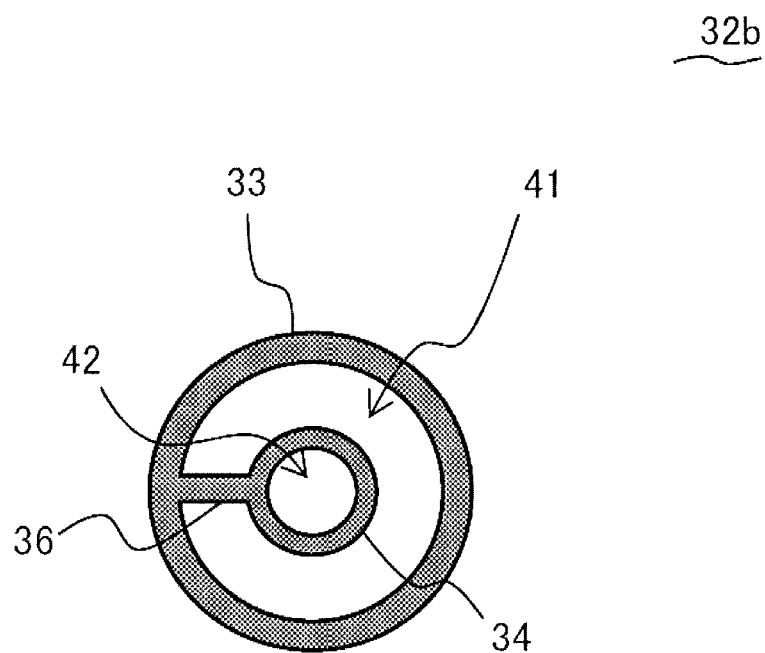
FIG. 11 is a section view of a gas supply beam probe of a surgery system according to a fourth embodiment.

FIG. 11 is a sectional view of a gas supply beam probe 32b of the surgery system according to the present embodiment. The surgery system according to the present embodiment is different from the surgery system 103 according to the second embodiment in that it includes a gas supply beam probe 32b illustrated in FIG. 11 instead of the gas supply beam probe 32. The gas supply probe beam 32b differs in that it includes a notch portion 36 connecting the outer tube 33 and the inner tube 34 in the conduit 41 between the outer tube 33 and the inner tube 34.

Also, with the surgery system and the gas delivery system according to the present embodiment as described above, the same effect can be obtained as in the surgery system 103 and the gas delivery system 103a according to second embodiment.

Furthermore, according to the surgery system and the gas delivery system according to the present embodiment, by providing the notch portion 36, it is possible to improve the strength of the gas supply beam probe 32b.

Figure 13:
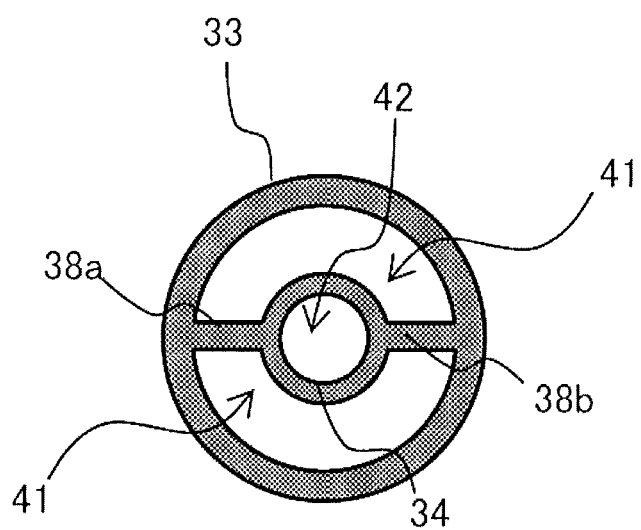
FIG. 13 is a section view of a gas supply beam probe of another modification of the surgery system according to the fourth embodiment.

The range in which the notch portion is formed in the conduit 41 between the outer tube 33 and the inner tube 34 may be within 50% of the outer region of the inner tube 34. Thus, for example, as illustrated in FIG. 12, a gas supply beam probe 32c having a notch portion 37 that is wider than the notch portion 36 of the gas supply beam probe 32b may be used. Further, as illustrated in FIG. 13, a gas supply beam probe 32d having a plurality of notch portions (notch portion 38a, notch portion 38b) may be used.

<Fifth Embodiment>

Figure 14:
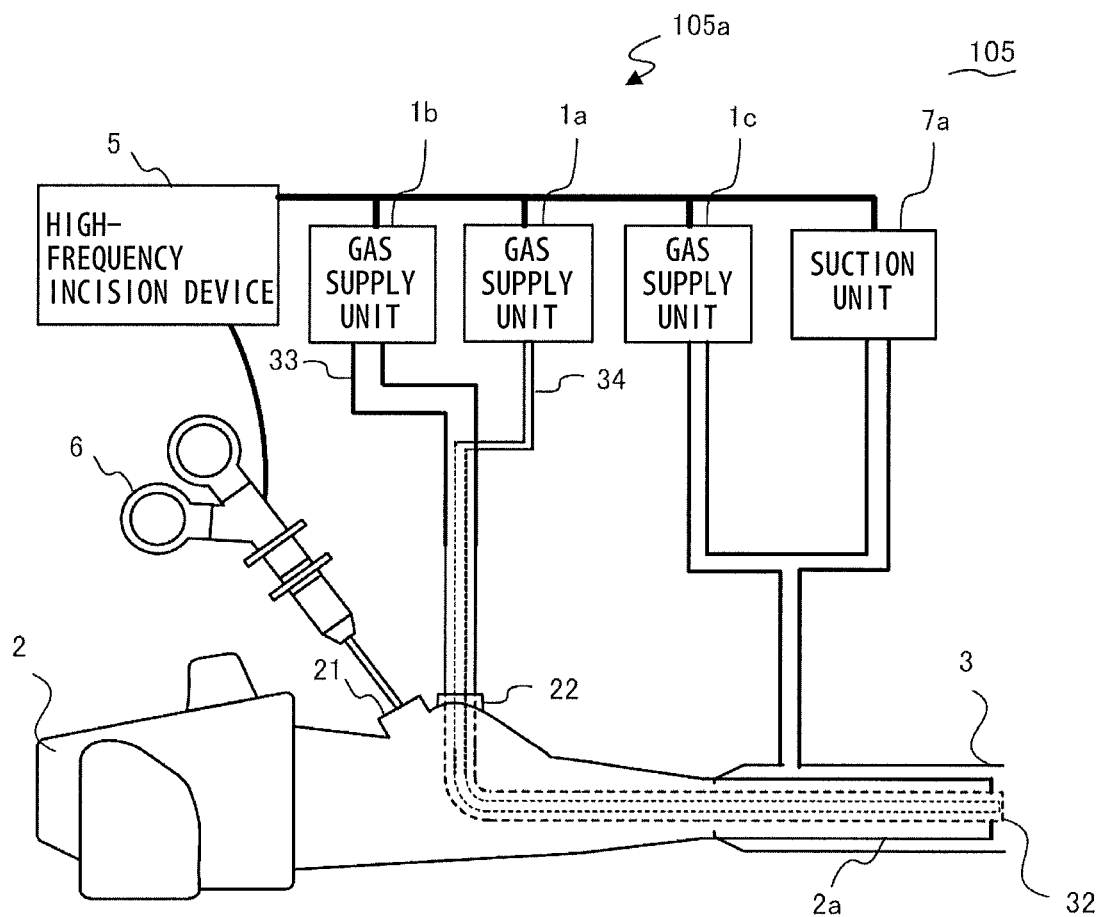
FIG. 14 is a diagram illustrating a portion of a configuration of a surgery system according to a fifth embodiment.
Figure 15:
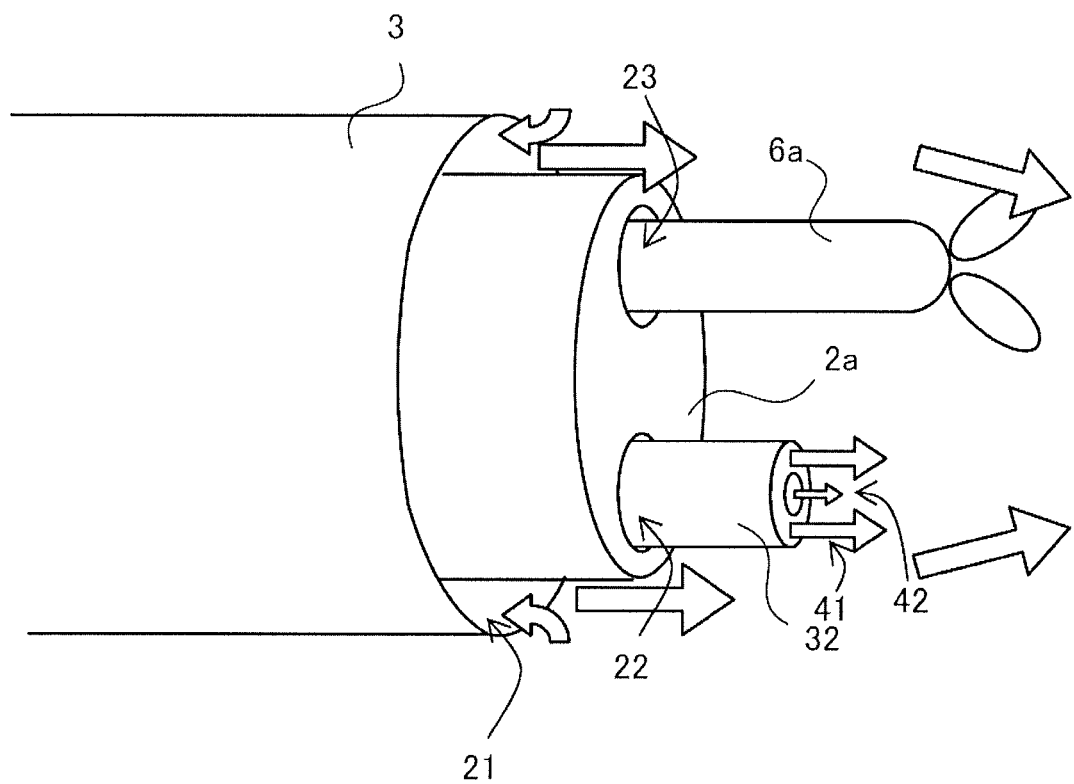
FIG. 15 is a partially enlarged view of the surgery system according to the fifth embodiment.

FIG. 14 is a diagram illustrating a portion of a configuration of a surgery system 105 according to the present embodiment. FIG. 15 is a partially enlarged view of the surgery system 105 according to the present embodiment.

The surgery system 105 according to the present embodiment is a surgery system that combines the overtube 3 according to the first embodiment and the gas supply beam probe 32 according to the second embodiment. The surgery system 105 is similar to the surgery system 100 according to the first embodiment in that it includes a gastrointestinal endoscope 2 that is a flexible endoscope in which two channels are formed, and in that a channel 23 of one of the channels in the gastrointestinal endoscope 2 is inserted with the treatment instrument 6 which is electrically connected to the high-frequency incision device 5, and, as illustrated in FIG. 15, the high-frequency probe 6a is introduced into the gastrointestinal lumen from the distal end of the insertion section 2a.

The surgery system 105 differs from the surgery system 100 according to the first embodiment, first of all in that the gas supply beam probe 32 is inserted into the other channel 22 of the gastrointestinal endoscope 2. The gas supply beam probe 32 inserted into the channel 22 is similar to the gas supply beam probe 32 according to the second embodiment. The inner tube 34 constituting the gas supply beam probe 32 is connected to the gas supply unit 1a, and the outer tube 33 is connected to the gas supply unit 1b.

The surgery system 105 further differs from the surgery system 100 according to the first embodiment in that a tube linking to the gas supply unit 1c and the suction unit 7a is connected to the overtube 3. When the gas supply unit 1c in the surgery system 105 is in operation, insufflation gas is supplied from the conduit 21, which is formed between the gas supply beam probe 32 and the overtube 3. On the other hand, when the suction unit 7a is in operation, the objects in the gastrointestinal lumen are aspirated from the conduit 21. Operation of the gas supply unit 1c and the suction unit 7a is carried out alternatively.

In the present embodiment, of the surgery system 105, mainly the gas supply device (gas supply unit 1, gas supply unit 1b, gas supply unit 1c), the gastrointestinal endoscope 2, the overtube 3, and the gas supply beam probe 32 constitute the gas delivery system 105a to realize the function of supplying gas. The gas delivery system 105a is connected to the high-frequency incision device 5 and the suction unit 7a. Also, the surgery system 105 is similar to the surgery system 100, in that it is structured such that insufflation gas is supplied automatically in conjunction with the operation of the high-frequency incision device 5 and the suction unit 7a.

As illustrated in FIG. 15, the insertion portion 2a and the overtube 3 form the conduit 21, which is a first conduit for supplying insufflation gas to the gastrointestinal lumen 4 from the gas supply unit 1c. Further, as illustrated in FIG. 15, the gas supply beam probe 32 has a dual structure provided with the outer tube 33 which is a first guide pipe extending from the gas supply unit 1b and the inner tube 34 which is a second guide pipe extending from the gas supply unit 1a. Then, the outer tube 33 and the inner tube 34 form a conduit 41, which is a second conduit to supply the gastrointestinal lumen 4 with the insufflation gas from the gas supply unit 1b, and the inner tube 34 forms a conduit 42, which is a third conduit to supply the gastrointestinal lumen 4 with the insufflation gas from the gas supply unit 1a. That is, the surgery system 105 and the gas system 105a have a triple structure of gas routes to provide insufflation gas to the gastrointestinal lumen 4.

In the surgery system 105 and the gas delivery system 105a as described above, the gas supply unit 1a and the gas supply unit 1b supply and send insufflation gas to the conduits 41 and 42 such that the flow velocity of the insufflation gas supplied from the conduit 41 formed between the outer tube 33 and the inner tube 34 is faster than the flow velocity of the insufflation gas supplied from the conduit 42 formed in the inner tube 34. Moreover, the gas supply unit 1b and the gas supply unit 1c supply and send insufflation gas to the conduits 21 and 41 such that the flow velocity of the insufflation gas supplied from the conduit 21, which is formed between the insertion portion 2a and the overtube 3, is faster than the flow velocity of the insufflation gas supplied to the conduit 41 formed between the outer tube 33 and the inner tube 34.

Therefore, as illustrated in FIG. 15, a difference in pressure is caused in the gastrointestinal lumen by the difference in the flow velocity of the insufflation gas from the conduit 41 and the insufflation gas from the conduit 42, and the insufflation gas from the conduit 41 is pulled inwardly. A difference in pressure is caused in the gastrointestinal lumen by the difference in the flow velocity of the insufflation gas from the conduit 21 and the insufflation gas from the conduit 41, and the insufflation gas from the conduit 21 is pulled inwardly. With this, the diffusion of the insufflation gas is suppressed to achieve a high linearity in the insufflation gas as a whole, thereby allowing the insufflation gas to be supplied to a greater distance.

Therefore, according to the surgery system 105 and the gas delivery system 105a, it is possible to make the supplied insufflation gas that is supplied to the narrow gastrointestinal lumen 4 reach the affected area more reliably, in the same manner as the surgery system 100 and the gas delivery system 100a according to the first embodiment. Otherwise, this embodiment is also similar to the surgery system 100 and the gas delivery system 100a according to the first embodiment, in that it is possible to reduce the operation load of the surgeon by automating the gas supply and the aspiration.

Further, the gas delivery system 105a and the surgery system 105 according to the present embodiment can supply insufflation gas at a higher flow rate than the surgery system 103 and the gas systems 103a according to the second embodiment, which performs supplying of gas with a single gas supply beam probe.

<Sixth Embodiment>

Figure 17:
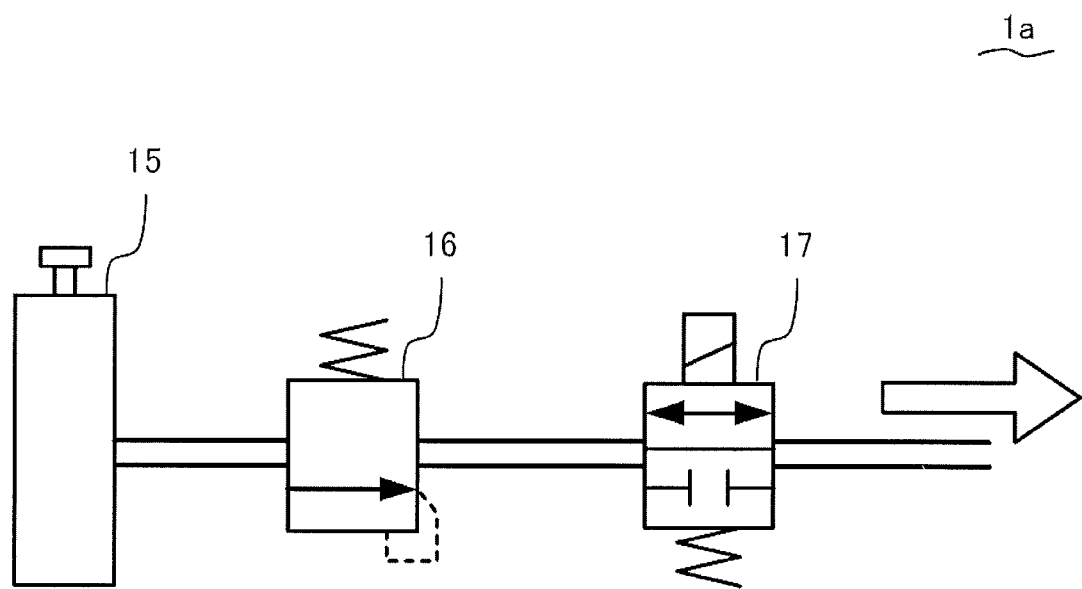
FIG. 17 is a diagram illustrating a configuration of a gas supply unit of the surgery system according to the sixth embodiment.
Figure 18:
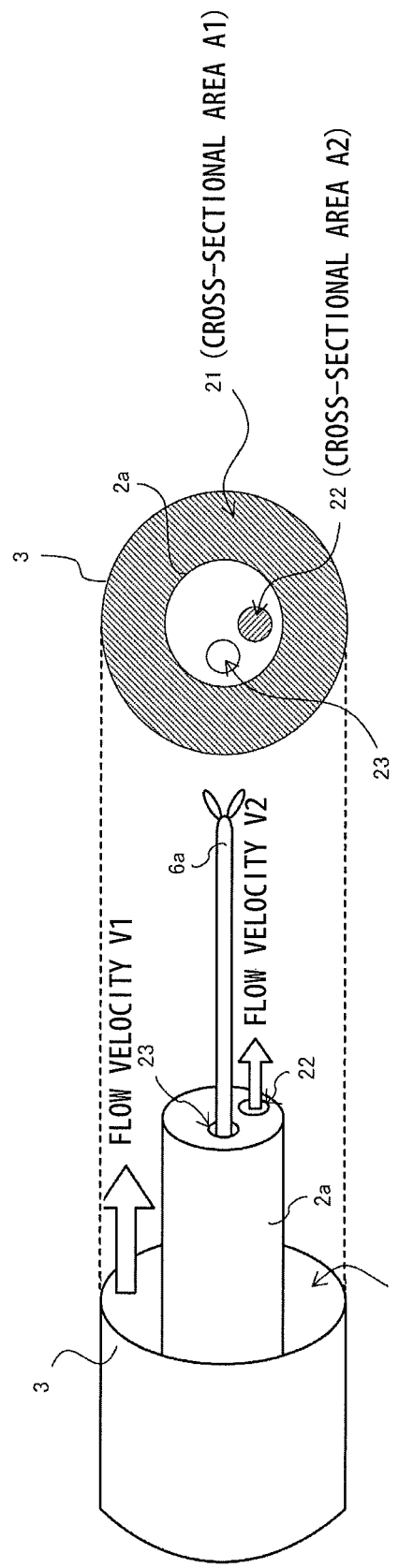
FIG. 18 is a partially enlarged view of the surgery system according to the sixth embodiment.
Figure 19:
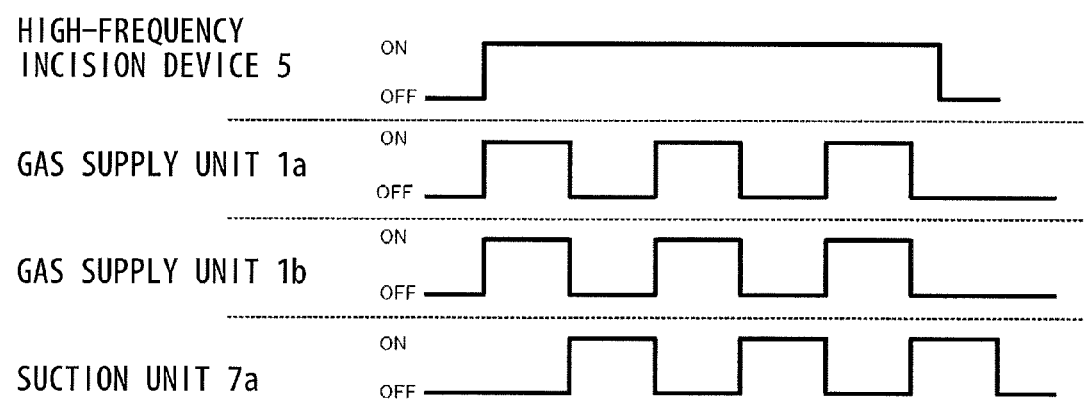
FIG. 19 is a diagram for explaining an operation timing of various devices of the surgery system according to the sixth embodiment.

FIG. 16 is a diagram illustrating a portion of a configuration of a surgery system 106 according to the present embodiment. FIG. 17 is a diagram illustrating a configuration of a gas supply unit of the surgery system 106 according to the present embodiment. FIG. 18 is a partial enlarged view of the surgery system 106 according to the present embodiment. FIG. 19 is a diagram for explaining the operation timings of various devices of the surgery system 106 according to the present embodiment.

The surgery system 106 according to the present embodiment differs from the surgery system 100 according to the first embodiment in that it includes a flow sensor 12a between the gas supply unit 1a and the channel 22, and in that it includes a flow sensor 12b between the gas supply unit 1b and suction unit 7a, and a gas supply port 24 of the overtube 3 consisting of a flexible member. The surgery system 106 further differs from the surgery system 100 according to the first embodiment in that it includes an interface unit 14 for the user to change the drive settings, and a control unit 13 that communicates with various units (gas supply unit 1, gas supply unit 1b, high-frequency incision device 5, suction unit 7a, flow sensor 12a, flow sensor 12b) of the surgery system 106 to which it is electrically connected for controlling the operation thereof.

Under the control of the control unit 13, the gas supply units 1a and 1b adjust the output (gas quantity). The configuration of the gas supply units 1a and 1b other than a configuration including a gas compressor may be configured to include, for example, a configuration including a gas supply source 15 for supplying high-pressure gas, a regulator 16 that decompresses a high-pressure gas and a proportional solenoid valve 17 for regulating the flow rate, as shown in FIG. 17.

The suction unit 7a is a means for generating a negative pressure, under the control of the control unit 13, to adjust the amount of aspiration by the negative pressure. For example, the suction unit 7a is provided with a vacuum pump such as a peristaltic pump or a rotary pump.

The flow sensors 12a and 12b are sensors for detecting the flow rate of insufflation gas flowing through the conduits in which the flow sensors are installed per unit time. The flow sensor 12a detects a gas supply quantity Q1, which is the flow rate of insufflation gas from the gas supply unit 1a. The flow sensor 12b detects a gas quantity Q2, which is the flow rate of insufflation gas from the gas supply unit 1b, and detects an aspiration flow rate Q3 to the suction unit 7a.

The control unit 13 carries out the detection of an output signal from the high-frequency incision device 5, the drive control of the gas supply unit (gas supply unit 1, gas supply unit 1b) and the suction unit 7a, the detection of an output from flow sensors (flow sensor 12a, flow sensor 12b), and the like. When the user operates the high-frequency incision device 5 in the surgery system 106, the high-frequency incision is started and a signal is transmitted to the control unit 13 from the high-frequency incision device 5. As illustrated in FIG. 19, the control unit 13, having received the signal, controls the gas supply unit 1a, the gas supply unit 1b, and the suction unit 7a so as to repeatedly perform supplying of gas by the gas supply unit 1a and the gas supply unit 1b, and aspiration by the suction unit 7a, at a timing as illustrated in FIG. 19. As a result, the gastrointestinal lumen 4 is ventilated Specifically, the control unit 13, having received the signal, first controls the gas supply unit 1a and the gas supply unit 1b to start supplying gas for diffusing the fumes produced in the gastrointestinal lumen 4 by high-frequency incision. At this time, as illustrated in FIG. 18, the control unit 13 controls the gas supply unit 1a and the gas supply unit 1b such that the flow velocity V1 of the insufflation gas supplied from the conduit 21 which is formed between the overtube 3 and the insertion portion 2a is faster than the flow velocity V2 of the insufflation gas supplied from the channel 22 formed in the gastrointestinal endoscope 2 (the insertion portion 2a).

Thus, the difference in pressure is caused by the difference between the flow velocity of the concentric circular insufflation gas from the conduit 21 and the insufflation gas from the channel 22, whereby the insufflation gas from the conduit 21 is pulled inwardly and flows to converge in the axial direction of the overtube 3. As a result, the diffusion of the insufflation gas is suppressed and it is possible to achieve a high linearity in the insufflation gas as a whole, thereby allowing the insufflation gas to reach a greater distance.

The point at which the control unit 13 controls the gas supply unit 1a and the gas supply unit 1b such that the flow velocity V1 is faster than the flow velocity V2 will be described in more detail.

As for the insufflation gas flowing inside the conduit, the following relation between the flow rate Q per time unit, the flow velocity V, and the cross-sectional surface A of the conduit is obtained: "flow rate Q=flow velocity V×cross-sectional surface A". In the surgery system 106, the flow rates Q1 and Q2 of the insufflation gas from the supply units 1a and 1b are known, because they are detected by the flow sensors 12a and 12b. In addition, the cross-sectional area A1 of the conduit 21 and the cross-sectional area A2 of the channel 22 are also known.

Therefore, in the surgery system 106, as illustrated in FIG. 18, by dividing the flow rate Q1 obtained by the flow sensor 12a with the cross-sectional area A1 of the conduit 21 which is formed between the overtube 3 and the insertion portion 2a, it is possible to determine the flow velocity V1 of the insufflation gas to be supplied to the gastrointestinal lumen 4 from the conduit 21. Further, by dividing the flow rate Q2 obtained by the flow sensor 12b with the cross-sectional area A2 of the channel 22 formed in the gastrointestinal endoscope 2 (insertion portion 2*a*), it is possible to obtain the flow velocity V2 of the insufflation gas that is supplied to the gastrointestinal lumen 4 from the channel 22.

Furthermore, in the surgery system 106, the flow velocity and the flow rate are proportional to each other, thus when the flow rate is increased then the flow velocity also increases, and when the flow rate is decreased then the flow velocity also decreases. From this it is evident that the control unit 13 can indirectly control the flow velocity by controlling the flow rate from the gas supply unit 1*a* and the gas supply unit 1*b*.

Accordingly, the control unit 13 controls the gas supply unit 1*a* and the gas supply unit 1*b*, such that the optimal flow rate obtaining the relationship of the flow velocity V1>the flow velocity V2 is achieved by feedback control of the output from the flow sensors, so that in the surgery system 106 the relationship of the flow velocity V1>the flow velocity V2 is realized.

It should be noted that the cross-sectional area A1 and the cross-sectional area A2 varies depending on the type of endoscope (flexible scope). Therefore, it is preferable to determine the cross-sectional area A1 and the cross-sectional area A2 used for calculation by storing beforehand the cross-sectional area A1 and the cross-sectional area A2 in the control unit 13 for each endoscope and by selecting the endoscope that the user will use from the interface unit 14.

After the gas supply has continued for a certain period of time, the control unit 13 stops the gas supply temporarily by controlling the gas supply unit 1*a* and the gas supply unit 1*b*, and starts aspiration by controlling the suction unit 7*a*. Aspiration is performed while diffusing the fumes resulting from a high-frequency incision of the affected area by supplying insufflation gas for a certain time. Therefore, fumes can be effectively discharged even when the aspiration position (i.e., the distal end of the overtube 3) is in a location remote from the affected area, and a good visual field of the endoscope can be ensured.

During the aspiration operation, the control unit 13 feedback controls the aspiration quantity Q3 detected by the flow quantity sensor 12*b*, such that the aspiration quantity Q3 per time unit detected by the flow sensor 12*b* is the sum of gas supply quantity Q1 and gas supply quantity Q2 per time unit during supplying of gas (that is, aspiration quantity Q3=gas supply quantity Q1+gas supply quantity Q2). Thus, the pressure in the gastrointestinal lumen 4 is kept constant.

According to the surgery system 106 and the gas delivery system 106*a*, as described above, it is possible to make the insufflation gas that is supplied to the narrow gastrointestinal lumen 4 reach the affected area more reliably in the same manner as the surgery system 100 and the gas delivery system 100*a*. Otherwise, this embodiment is similar to the gas delivery system 100*a* and the surgery system 100 according to the first embodiment, in that it is possible to reduce the operation load of the surgeon by automating the gas supply and the aspiration.

Further, in the gas delivery system 106*a* and the surgery system 106 according to the present embodiment, the cross-sectional area A1 and the cross-sectional area A2 for each gastrointestinal endoscope is determined, and accordingly, on the basis of the output from the flow sensor 12*a* and the flow sensor 12*b*, the gas supply quantity is controlled by feedback control so as to maintain the relationship of flow velocity V1>flow velocity V2. Therefore, it is possible regardless of the endoscope to ensure the linearity of the insufflation gas securely. Further, on the basis of the output from the flow sensor 12*b*, the aspiration quantity is controlled by feedback control such that the aspiration quantity Q3 becomes equal to gas supply quantity Q1+gas supply quantity Q2. Therefore, it is possible to suppress fluctuations in pressure in the gastrointestinal lumen 4 via gas supply and aspiration to maintain a constant pressure in the gastrointestinal lumen 4. That is, in the surgery system 106 and the gas delivery system 106*a* according to the present embodiment, it is possible to optimally control the flow rate on the basis of the output from the flow sensors.

What is claimed is:

1. A gas delivery system for supplying a body cavity with a given gas, the gas delivery system comprising:
   a first flow sensor;
   a second flow sensor different from the first flow sensor;
   a first guide pipe to be inserted into the body cavity;
   a second guide pipe installed inside the first guide pipe;
   a first conduit supplying the body cavity with a first gas at a first flow velocity measured by the first flow sensor, the first conduit being disposed between the first guide pipe and a portion of the second guide pipe installed inside the first guide pipe; and
   a second conduit supplying the body cavity with a second gas at a second flow velocity measured by the second flow sensor, the second conduit being disposed inside the portion of the second guide pipe installed inside the first guide pipe;
   a gas supply unit that includes a first gas supply unit and a second gas supply unit, the first gas supply unit supplying the first gas to the first conduit, the second gas supply unit supplying the second gas to the second conduit; and
   a controller programmed to:
      control the gas supply unit such that the first flow velocity of the first gas that is supplied from the first conduit becomes higher than the second flow velocity of the second gas that is supplied from the second conduit based on: (i) an output from the first flow sensor disposed between the first gas supply unit and the first conduit, and (ii) an output from the second flow sensor disposed between the second gas supply unit and the second conduit.

2. The gas delivery system according to claim 1, wherein the first guide pipe is an overtube into which an insertion portion of an endoscope is inserted for observing the body cavity, and
   the second guide pipe is the insertion portion of the endoscope to be inserted into the overtube.

3. The gas delivery system according to claim 2, wherein the gas supply unit is configured such that the first or second gas is supplied while alternately performing aspiration of objects in the body cavity by a suction unit connected to the gas delivery system.

4. The gas delivery system according to claim 3, further comprising:
   a first valve provided on a gas supply route from the gas supply unit to the first conduit for regulating the first flow velocity; and
   a second valve provided on a gas supply route from the gas supply unit to the second conduit for regulating the second flow velocity.

5. A surgery system comprising:
   the gas delivery system according to claim 3; and
   the suction unit connected to the gas delivery system.

6. The surgery system according to claim 5, wherein the suction unit is configured to aspirate objects in the body cavity from at least one of the first conduit and the second conduit.

7. The gas delivery system according to claim 1, wherein the first guide pipe and the second guide pipe are inserted into a channel of an endoscope.

8. The gas delivery system according to claim 7, wherein the gas supply unit is configured such that the first or second gas is supplied while alternately performing aspiration of objects in the body cavity by a suction unit connected to the gas delivery system.

9. A surgery system comprising:
the gas delivery system according to claim 8; and
the suction unit connected to the gas delivery system.

10. The surgery system according to claim 9, wherein the suction unit is configured to aspirate objects in the body cavity from at least one of the first conduit and the second conduit.

11. The gas delivery system according to claim 8, further comprising:
a first valve provided on a gas supply route from the gas supply unit to the first conduit for regulating the first flow velocity; and
a second valve provided on a gas supply route from the gas supply unit to the second conduit for regulating the second flow velocity.

12. A surgery system comprising:
the gas delivery system according to claim 1; and
a suction unit connected to at least one of the first and second conduits of the gas delivery system, wherein:
the gas supply unit is configured to supply the first or second gas from at least one of the first and second conduits connected to the suction unit while alternatively performing aspiration of objects in the body cavity by the suction unit.

* * * * *